(12) United States Patent
Reyes et al.

(10) Patent No.: US 6,638,229 B2
(45) Date of Patent: Oct. 28, 2003

(54) IMAGE PRODUCING APPARATUS

(76) Inventors: Lionel Reyes, 16 Kirkley Drive, Heanor, Derbyshire, DE75 7UR (GB); Geoffrey Clarke Shand, 5 Bromyard Drive, Chellaston, Derby, DE73 1PF (GB); Cesare Giovanni Giorgi, 53 Foro Buonaparte, I-20100, Milano (IT)

( * ) Notice: Subject to any disclaimer, the term of this patent is extended or adjusted under 35 U.S.C. 154(b) by 0 days.

(21) Appl. No.: 09/978,820

(22) Filed: Oct. 15, 2001

(65) Prior Publication Data

US 2002/0049380 A1 Apr. 25, 2002

(30) Foreign Application Priority Data

Oct. 19, 2000 (GB) .............................. 0025646

(51) Int. Cl.[7] .................................. A61B 8/00
(52) U.S. Cl. ...................................... 600/446
(58) Field of Search ........................... 600/437, 439, 600/443, 445–447, 459–471

(56) References Cited

U.S. PATENT DOCUMENTS

| | | | | |
|---|---|---|---|---|
| 4,137,777 A | * | 2/1979 | Haverl et al. | 73/620 |
| 4,185,501 A | * | 1/1980 | Proudian et al. | 73/641 |
| 4,315,435 A | * | 2/1982 | Proudian | 73/628 |
| 4,893,628 A | * | 1/1990 | Angelsen | 600/441 |
| 5,107,844 A | * | 4/1992 | Kami et al. | 600/463 |
| 5,282,472 A | * | 2/1994 | Companion et al. | 600/463 |
| 5,377,682 A | * | 1/1995 | Ueno et al. | 600/463 |
| 5,651,366 A | * | 7/1997 | Liang et al. | 600/463 |
| 5,720,287 A | * | 2/1998 | Chapelon et al. | 600/439 |

* cited by examiner

Primary Examiner—Francis J. Jaworski
(74) Attorney, Agent, or Firm—Smith-Hill and Bedell

(57) ABSTRACT

Image producing apparatus 10, 100 comprising means 48, 112 for producing and also receiving an ultrasound signal, the apparatus being arranged such that a plurality of ultrasound signals are sequentially produced in different directions to cover a volume of a required shape, with the signals received being analyzed to provide a three dimensional image of the volume.

43 Claims, 3 Drawing Sheets

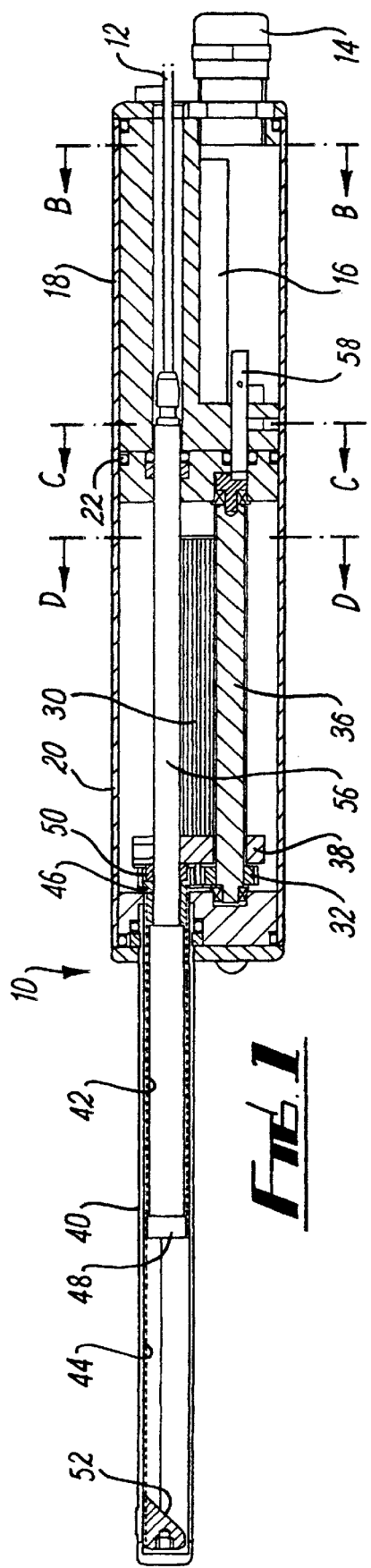
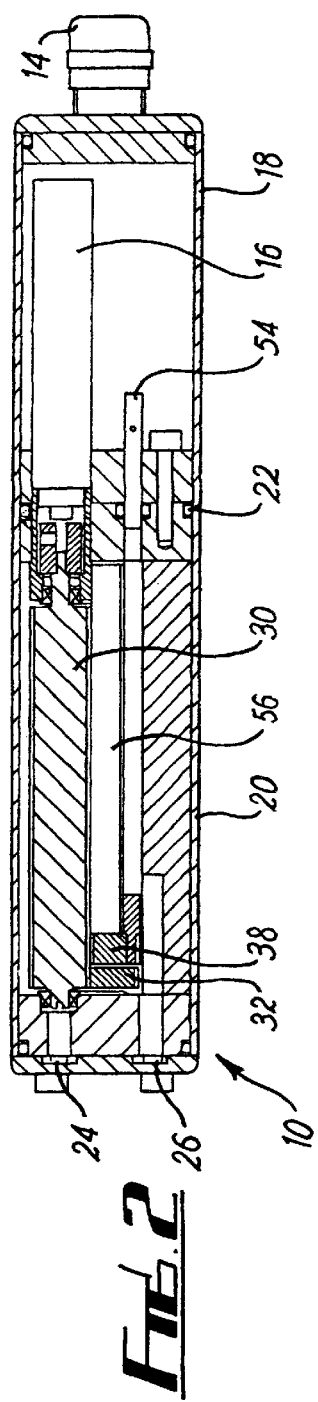
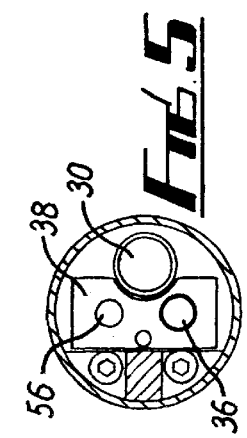
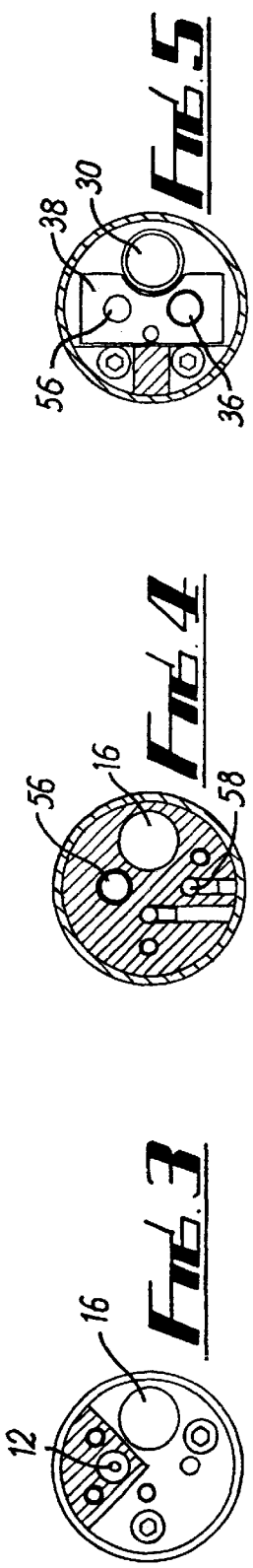
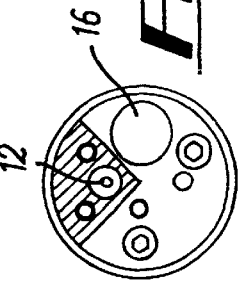

IMAGE PRODUCING APPARATUS

This invention concerns image producing apparatus, and particularly but not exclusively such apparatus usable in surgery, and especially neurosurgery.

Computer assisted surgery is an important tool for minimally invasive procedures. It allows for planning procedures before an operation, and is usually based upon a three dimensional image of the anatomy produced beforehand, for instance by magnetic resonance imaging. However, where the anatomical substrate is soft and affected by a patients position during surgery, the initial images obtained are of limited use as organs in the body will have moved. This is particularly the position in neurosurgery where for instance it may be required to remove a tumour, but where it is highly significant not to remove surrounding live tissue.

According to the present invention there is provided image producing apparatus, the apparatus comprising means for producing and also receiving an ultrasound signal, the apparatus being arranged such that a plurality of ultrasound signals are sequentially produced in different directions, the apparatus also comprising means for analysing the ultrasound signals produced and received so as to produce a three dimensional image therefrom.

The apparatus preferably comprises a single ultrasound signal producing and receiving means, which may comprise a piezo element.

The apparatus may comprise a reflecting mirror for reflecting the ultrasound signals. The reflecting mirror may be movable within the apparatus. The reflecting mirror may be rotationally movable, and may also be linearly movable. The ultrasound signal producing and receiving means and reflecting mirror are preferably maintained in a constant spaced relationship with the apparatus.

In one embodiment the ultrasound signal producing and receiving means is movable within the apparatus. The ultrasound signal producing and receiving means may be linearly movable.

The ultrasound signal producing and receiving means, and reflecting mirror, are preferably provided respectively on first and second movable concentric cylindrical members, which members are rotatable relative to each other. A one of the cylindrical members preferably extends at least partially within the other. The ultrasound signal producing and receiving means may be provided on the inner cylindrical member.

The reflecting mirror is preferably movable in a generally helical path.

The two cylindrical members are preferably movable by a common rotational drive. The cylindrical member bearing the ultrasound signal producing and receiving means may engage with a helically threaded member rotatable by the common drive, with means preventing rotation of said cylindrical member. The cylindrical member bearing the reflecting mirror may rotatably engage with an elongate gear rotatable by the common drive. Said cylindrical member bearing the reflecting mirror may be linearly movable by the other cylindrical member.

The apparatus may be arranged to produce an image of a substantially cylindrical volume.

In an alternative arrangement a second mirror may be provided for reflecting the ultrasound signals downstream of the reflecting mirror. The second mirror may be pivotally movable relative to the reflecting mirror and may be pivotal by virtue of a cam arrangement. The apparatus may be arranged to produce an image of a substantially frusto conical volume.

The apparatus preferably comprises a housing which locates the ultrasound producing and receiving means, and means for moving same. A part of the housing is preferably liquid tight such that an ultrasound liquid couplant can be contained therein.

The apparatus preferably comprises a motor for moving the movable parts of the apparatus. The motor which may be a d.c. motor, is preferably located outside of the liquid tight part of the housing.

The apparatus preferably comprises means for detecting the position of the ultrasound signal producing and receiving means relative to at least said receiving mirror, said detecting means being operatively connected to the analysing means. One or more position sensors may be provided, and the sensors may comprise inductive switches. The sensors may detect both linear and rotational movement, and an inductive switch may be provided to detect linear movement. An inductive switch which detects the relative rotational position of a member rotatable by the common drive may also be provided.

The housing may comprise a projecting part which is significantly narrower than the remainder of the housing, and which projecting part locates the ultrasound signal producing and receiving means.

The analysing means may convert signals received from the ultrasound signal producing and receiving means from analogue to digital signals. The analysing means may be arranged such that once a three dimensional image has been produced, this image is automatically updated by further signals received.

Embodiments of the present invention will now be described by way of example only and with reference to the accompanying drawings, in which:

FIG. 1 is a diagrammatic sectional side view of part of a first apparatus according to the invention;

FIG. 2 is a diagrammatic sectional plan view of part of the apparatus of FIG. 1;

FIGS. 3 to 5 are respectively cross-sectional views along the lines B—B, C—C and D—D of FIG. 1;

Figure 6:
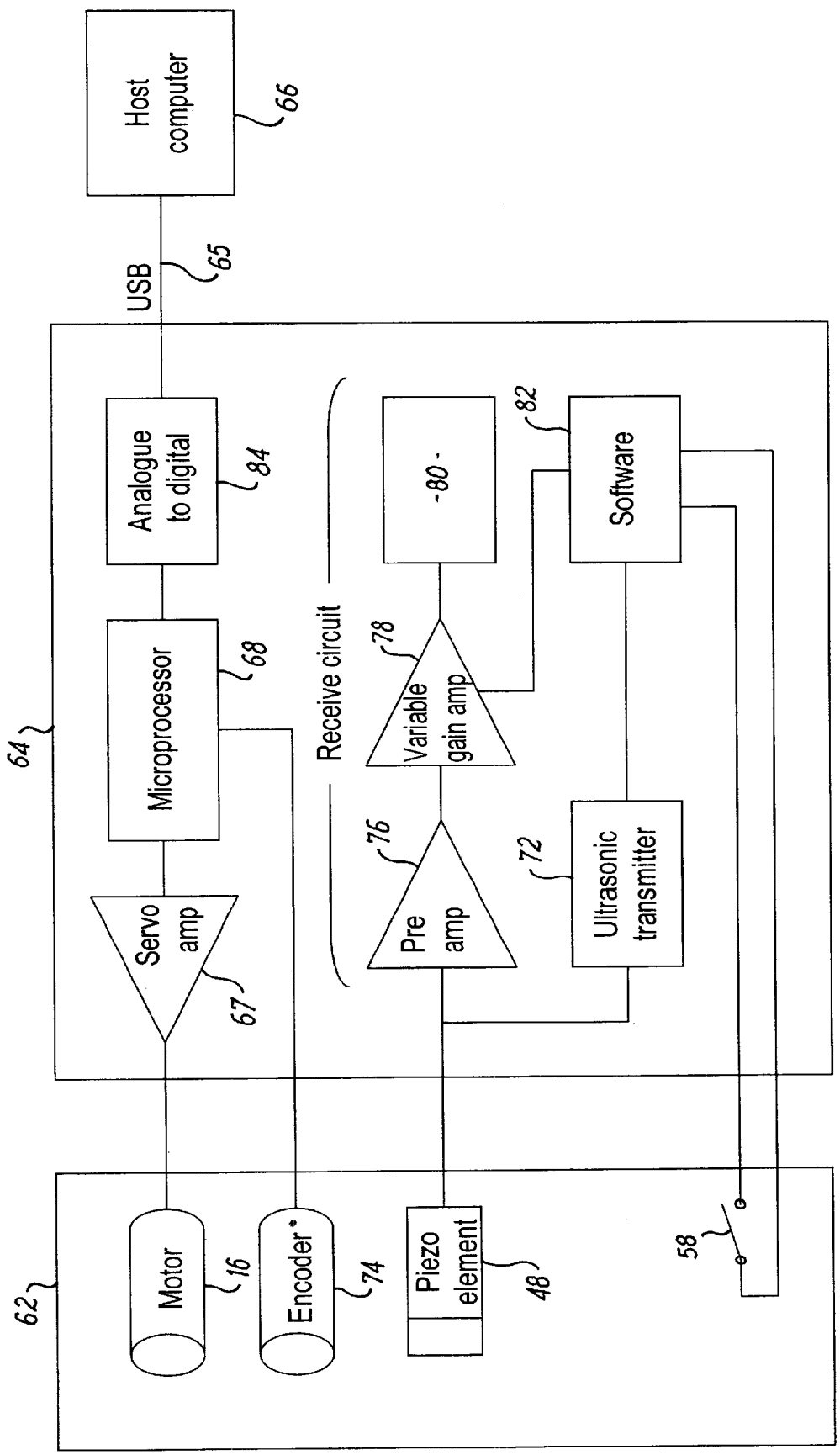
FIG. 6 is a block diagram illustrating operation of the apparatus of FIG. 1.

FIGS. 1 to 5 show part of a first ultrasound scanning apparatus 10 according to the invention which in use would be connected by a cable 12 to analysing apparatus, which is not shown but will be described with reference to FIG. 6. A further port 14 is provided on an other side of the apparatus 10 to receive an electrical current to power a d.c. motor and encoder 16 and other parts of the apparatus.

The apparatus 10 comprises a cylindrical main housing 18 which comprises a front fluid tight chamber 20 closed by a seal 22, and having a vent 24 and filler 26. The motor 16 is located rearwardly outside of the chamber 20 adjacent thereto.

The motor 16 drives an elongate gear 30 which extends for the length of the chamber 20. The elongate gear 30 inter alia engages with connecting gears 32 which drive a helically threaded shaft 36 which extends longitudinally for a substantial part of the chamber 20. The helically threaded shaft 36 engages with a threaded non-rotatable block 38 such that rotation of the shaft 36 causes the block 38 to respectively move within the chamber 20.

An elongate relatively narrow passage 40 extends from the chamber 20. A pair of concentric cylindrical members 42, 44 slidingly locate within the passage 40. The inner of the members 42 is mounted by a collar 46 to the block 38 such that rotation of the shaft 36 causes linear movement of the member 42 along the passage 40. The inner member 42 mounts a piezo element 48 connected to a coaxially mounted ultrasound probe 56 which connects to the cable 12.

The outer member 44 engages on the top of the collar 46, and so is linearly moveable with the inner member 42. The outer member 44 also engages via a gear 50 with the long gear 30 such that rotation of the gear 30 causes rotation of the outer member 44. The long gear 30 is of course interconnected to the shaft 36 such that when the motor 16 is driven the gear 30 and shaft 36 simultaneously rotate causing rotational and longitudinal movement of the outer member 44.

A mirror 52 for ultrasound is provided across an upper part of the member 44 at an inclination relative thereto. The mirror 52 is made of steel. The passage 40 has an exterior through which ultrasound can pass, and in this instance is made of perspex (registered trade mark).

An induction switch 54 is provided to detect the relative longitudinal position of the collar 46. A further induction switch 58 detects the relative rotational position of the outer member 44 and in particular the mirror 52.

In operation the motor 16 is driven such that the members 42, 44 are driven up and down the passage 40, with the outer member 44 and hence mirror 52 being simultaneously rotated such that ultrasound bursts can be applied to a three dimensional substantially cylindrical volume around the passage 40. The inductive switches will detect when an upper or lower part of the cycle is reached and automatically cause the motor 16 to reverse.

The apparatus also comprises analysing means most of which is not shown in FIGS. 1 to 5, but will now be described in relation to operation of the apparatus. The apparatus 10 illustrated in FIGS. 1 to 5 is shown broadly in FIG. 6 by box 62. The control system for the scanner apparatus 10 comprises an electronic interface box 64 that houses the motor drive system, ultrasonic transmitter and receive signal processing, analogue to digital conversion circuits and the timing generation circuits. The resultant digital data is passed to the control computer via a USB (Universal Serial Bus) Interface.

The motor drive system drives the d.c. motor 16 using a d.c. servo loop with a servo amp 67 to maintain a constant scan velocity. The demand voltage is generated by a microprocessor 68 under the control of the software in the electronic interface box 64. The microprocessor 68 monitors the position of the mirror 52 by monitoring the quadrature encoder mechanically linked to the scanning mechanism. The inductive limit switches 58 provide an absolute reference and pass a signal to the microprocessor 68.

An ultrasonic transmitter 72 generates a high voltage pulse, which can be varied but is nominally 50 ns wide, that excites the piezo element 48 and causes it to emit a burst of ultrasound, the generation being synchronised to the pulses from the encoder 74 in the apparatus 10. The circuit is designed to ensure that the voltage pulse contains no frequency components that may interfere with the weak received signal.

The weak received signal is amplified by a low noise pre-amplifier 76 to boost the signal level, followed by a variable gain amplifier 78, which sets the gain depending on the application. Analogue filtering is used to improve the signal to noise ratio after which the signal is rectified. Logarithmic rectification is used to accommodate the wide range of signal amplitudes being received. The functioning of both the transmitter 72 and receive circuit 76, 78, 80 are controlled by software 82 via signals sent down the USB 65 from the host computer 66.

The received signals are converted from analogue to digital at 84 in the electronic interface box, and the conversion is 8 bit at 25 Mhz. The software, via the USB bus 65 reads the digitised signal that is then stored for display at the end of the scan.

The main data acquisition program allows real time A-scan to be viewed so that the analogue perimeters, such as a gain and gate (time interval over which data is collected) to be set. After the inspection start and end point have been set, the scanner is datumed and data is acquired. After the acquisition, the data is displayed such that vertical and horizontal slices can be viewed. The display may with suitable software provide a three dimensional display.

In use for example in neurosurgery, the apparatus can be used at any time to provide an image for instance of a tumour being operated on, which could be compared with preoperative images. This could be shown on a screen visible by a surgeon to permit accurate surgical techniques to be carried out.

There is thus described apparatus usable for instance in neurosurgery to provide an essentially instant and up to date image during surgery and thereby permitting accurate surgery to be carried out, thus reducing the chances of live tissue being removed or parts of a tumour remaining. Whilst described in relation to this particular application, apparatus according to the invention could be used in a wide variety of different operational fields, as well as fields outside of surgery.

Figure 7:
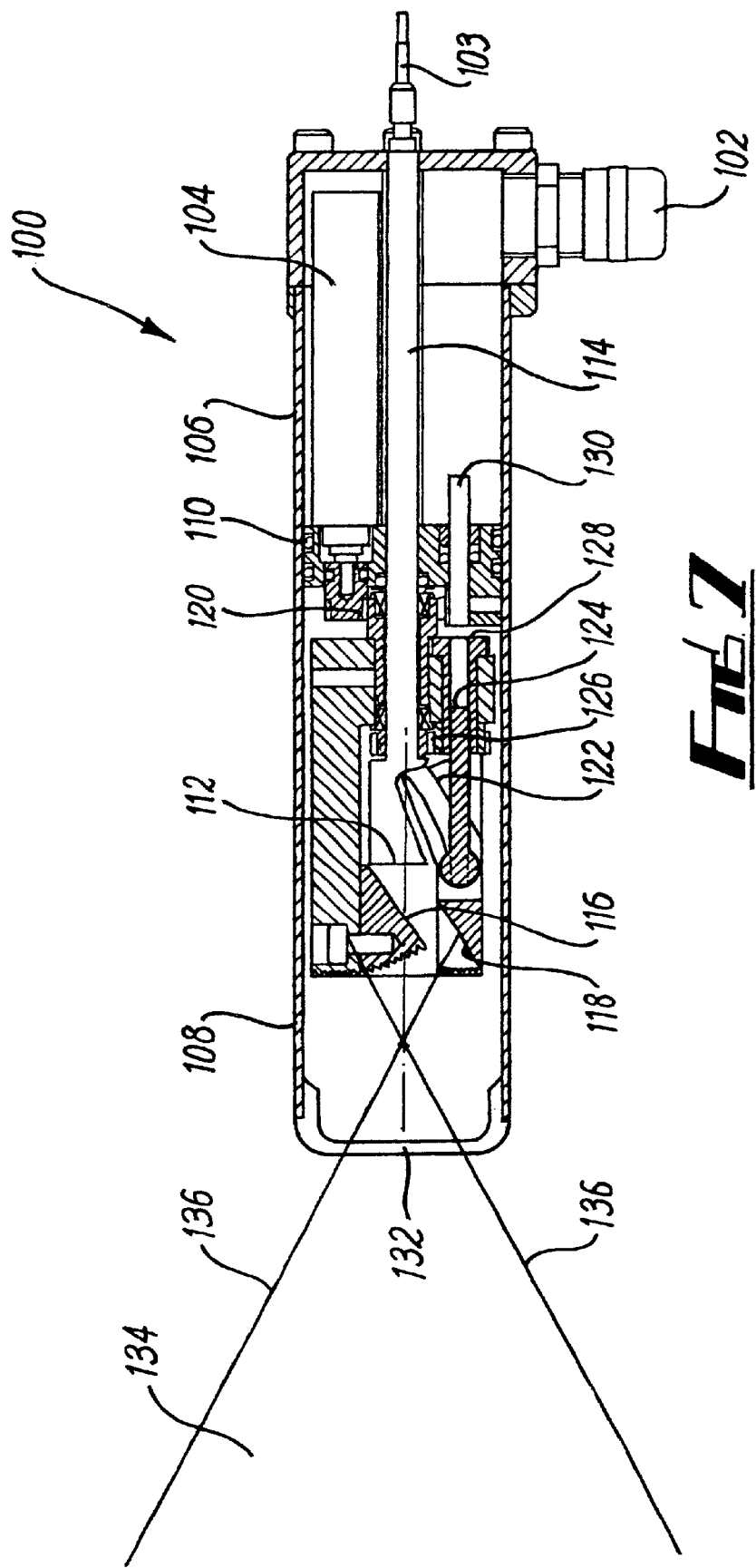
FIG. 7 is a diagrammatic sectional side view of part of a second apparatus according to the invention.

FIG. 7 shows part of a second ultrasound scanning apparatus 100 according to the invention. The apparatus 100 is similar in many aspects to the apparatus 10 and only the differences will be described in any detail. The principal difference between the apparatus 10 and the apparatus 100 being that in the latter the ultrasound probe, piezo element and mirrors etc. are not linearly movable.

In more detail the apparatus 100 comprises a cable 103 for connection to similar analysing apparatus as used with the apparatus 10, and a port 102 for connection to an electrical current to power a d.c. motor and encoder 104. The apparatus 100 again comprises a cylindrical main housing 106 with a front fluid tight chamber 108 closed by a seal 110.

A piezo crystal 112 is provided connected to an ultrasound probe 114. The crystal 112 is orientated to transmit and receive ultrasound signals onto a rotating mirror 116. The rotating mirror 116 is positioned to direct to and receive signals from a further pivoting mirror 118.

The mirrors 116,118 are rotatable relative to the probe by virtue of a gear drive 120 connected to the motor 104. The mirror 118 is pivotal by virtue of a cam 122 engageable with a lead screw 124 engageable with a further gear drive 126, the lead screw 124 being engageable with a rotating nut 128. An inductive switch 130 is provided to detect the position of the pivoting mirror 118.

In use the apparatus 100 operates in a similar manner to the apparatus 10 with ultrasound signals being transmitted and passing through a perspex window 132 at the left hand end shown in FIG. 7 of the casing 108. The arrangement of the mirrors 116,118 provide for detection of an image in a frusto conical volume 134 as shown by the lines 136. The apparatus 100 is ideally suited for use in neurosurgery for confirming the precise position of a tumour.

It is to be realised that various other modifications may be made without departing from the scope of the invention. It may for instance be possible to rotate the ultrasound signal producing means, though it is found to be highly advantageous for the mirror to be moved, which permits reliable and easy electrical connection to the piezo element. Different means may be provided for movement of the element and/or mirror.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

What is claimed is:

1. Image producing apparatus, the apparatus comprising means for producing and also receiving an ultrasound signal, a reflecting mirror for reflecting ultrasound signals, first and second moveable concentric cylindrical members for mounting said ultrasound signal producing and receiving means and said reflecting mirror respectively, means for rotating said second cylindrical member within the apparatus and relative to the first cylindrical member, the first cylindrical member being substantially rotationally fixed within the apparatus, the apparatus being arranged such that a plurality of ultrasound signals are sequentially produced in different directions, and the apparatus also comprising means for analysing the ultrasound signals produced and received so as to produce a three dimensional image therefrom.

2. Apparatus according to claim 1, wherein the apparatus comprises a single ultrasound signal producing and receiving means.

3. Apparatus according to claim 2, wherein the ultrasound signal producing and receiving means comprises a piezo element.

4. Apparatus according to claim 1, wherein means are provided for linearly moving said mirror within said apparatus.

5. Apparatus according to claim 1, wherein means are provided for maintaining said ultrasound signal producing and receiving means in a constant spaced relationship within said apparatus.

6. Apparatus according to claim 1, wherein means are provided for linearly moving said ultrasound signal producing and receiving means within said apparatus.

7. Apparatus according to claim 1, wherein a one of the cylindrical members extends at least partially within the other.

8. Apparatus according to claim 7, wherein said ultrasound signal producing and receiving means are provided on said inner one of said cylindrical members.

9. Apparatus according to claim 1, wherein a common rotational drive is provided for moving said cylindrical members.

10. Apparatus according to claim 9, wherein a helically threaded member is provided which is rotatable by said common drive, said threaded member bearing said first cylindrical member, with means being provided to prevent rotation of said first cylindrical member.

11. Apparatus according to claim 10, wherein means are provided for moving said reflecting mirror in a generally helical path.

12. Apparatus according to claim 9, wherein an elongate gear rotatable by said common drive is provided, said elongate gear being rotatably engageable with said second cylindrical member.

13. Apparatus according to claim 9, wherein means are provided which causes said first cylindrical member to linearly move said second cylindrical member.

14. Apparatus according to claim 1, wherein the apparatus is arranged to produce an image of a substantially cylindrical volume.

15. Apparatus according to claim 1, wherein the apparatus comprises a housing which locates the ultrasound producing and receiving means, and means for moving same.

16. Apparatus according to claim 15, wherein a part of the housing is liquid tight such that an ultrasound liquid couplant can be contained therein.

17. Apparatus according to claim 15, wherein the housing comprises a projecting part which is significantly narrower than the remainder of the housing, and which projecting part locates the ultrasound signal producing and receiving means.

18. Apparatus according to claim 1, wherein said apparatus comprises a motor for moving parts of the said apparatus.

19. Apparatus according to claim 18, wherein said motor is a d.c. motor.

20. Apparatus according to claim 18, wherein a part of the housing is liquid tight such that an ultrasound liquid couplant can be contained therein and said motor is located outside of said liquid tight part of said housing.

21. Apparatus according to claim 1, wherein said apparatus comprises means for detecting the position of the ultrasound signal producing and receiving means relative to at least said receiving mirror, means being provided for operatively connecting said detecting means to said analysing means.

22. Apparatus according to claim 21, wherein said detecting means comprises position sensors.

23. Apparatus according to claim 22, wherein said position sensors comprise inductive switches.

24. Apparatus according to claim 22, wherein said position sensors detect both linear and rotational movement.

25. Apparatus according to claim 1, wherein the analysing means converts signals received from the ultrasound signal producing and receiving means from analogue to digital signals.

26. Apparatus according to claim 1, wherein the analysing means is arranged such that once a three dimensional image has been produced, this image is automatically updated by further signals received.

27. Image producing apparatus, the apparatus comprising means for producing and also receiving an ultrasound signal, a first reflecting mirror for reflecting the ultrasound signal, means for rotationally moving said mirror within said apparatus, a second mirror positioned to reflect signals from and to the first mirror and rotatable with the first mirror, means for pivotally moving said second mirror relative to said first mirror so that a plurality of ultrasound signals are sequentially produced in different directions, and means for analysing the ultrasound signals produced and received so as to produce a three dimensional image of a substantially frusto conical volume therefrom.

28. Apparatus according to claim 27, wherein the apparatus comprises a single ultrasound signal producing and receiving means.

29. Apparatus according to claim 28, wherein the ultrasound signal producing and receiving means comprises a piezo element.

30. Apparatus according to claim 27, wherein means are provided for maintaining said ultrasound signal producing and receiving means in a constant spaced relationship within said apparatus.

31. Apparatus according to claim 27, wherein said pivotal moving means comprises a cam arrangement.

32. Apparatus according to claim 27, wherein the apparatus comprises a housing which locates the ultrasound producing and receiving means, and means for moving same.

33. Apparatus according to claim 32, wherein a part of the housing is liquid tight such that an ultrasound liquid couplant can be contained therein.

34. Apparatus according to claim 32, wherein the housing comprises a projecting part which is significantly narrower than the remainder of the housing, and which projecting part locates the ultrasound signal producing and receiving means.

35. Apparatus according to claim 27, wherein said apparatus comprises a motor for moving parts of the said apparatus.

36. Apparatus according to claim 35, wherein said motor is a d.c. motor.

37. Apparatus according to claim 35, wherein a part of the housing is liquid tight such that an ultrasound liquid couplant can be contained therein and said motor is located outside of said liquid tight part of said housing.

38. Apparatus according to claim 27, wherein said apparatus comprises means for detecting the position of the ultrasound signal producing and receiving means relative to at least said receiving mirror, means being provided for operatively connecting said detecting means to said analysing means.

39. Apparatus according to claim 38, wherein said detecting means comprises position sensors.

40. Apparatus according to claim 39, wherein said position sensors comprise inductive switches.

41. Apparatus according to claim 39, wherein said position sensors detect both linear and rotational movement.

42. Apparatus according to claim 38, wherein the analysing means converts signals received from the ultrasound signal producing and receiving means from analogue to digital signals.

43. Apparatus according to claim 27, wherein the analysing means is arranged such that once a three dimensional image has been produced, this image is automatically updated by further signals received.

* * * * *